(12) United States Patent
Boyce et al.

(10) Patent No.: US 11,357,645 B2
(45) Date of Patent: Jun. 14, 2022

(54) IMPLANT WITH GRADED RADIOPACITY CALIBRATION FEATURE

(71) Applicant: Warsaw Orthopedic, Inc., Warsaw, IN (US)

(72) Inventors: Todd Boyce, Collierville, TN (US); Gretchen S. Selders, Memphis, TN (US); Matthew M. Morrison, Cordova, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 16/851,857

(22) Filed: Apr. 17, 2020

(65) Prior Publication Data
US 2021/0322186 A1 Oct. 21, 2021

(51) Int. Cl.
*A61F 2/46* (2006.01)
*A61F 2/44* (2006.01)
*A61F 2/30* (2006.01)

(52) U.S. Cl.
CPC .......... *A61F 2/4657* (2013.01); *A61F 2/4455* (2013.01); *A61F 2002/3008* (2013.01); *A61F 2002/30056* (2013.01); *A61F 2002/4661* (2013.01)

(58) Field of Classification Search
CPC ...... A61F 2/44; A61F 2/30; A61F 2002/3008; A61F 2250/0032; A61F 2250/0098
See application file for complete search history.

(56) References Cited

U.S. PATENT DOCUMENTS

| | | |
|---|---|---|
| 6,320,931 B1 | 11/2001 | Arnold |
| 6,790,233 B2 | 9/2004 | Brodke et al. |
| 7,326,251 B2 | 2/2008 | McCombe et al. |
| (Continued) | | |

FOREIGN PATENT DOCUMENTS

| | | |
|---|---|---|
| JP | 2008266528 A | 10/1996 |
| KR | 100479207 B1 | 3/2005 |
| WO | 2004006811 A2 | 1/2004 |

OTHER PUBLICATIONS

PCT/US2021/023108 International Search Report dated Jul. 9, 2021.
(Continued)

*Primary Examiner* — Anu Ramana
(74) *Attorney, Agent, or Firm* — Fox Rothschild LLP; P. Marshall Ticer (57) ABSTRACT

An implant device for use in achieving spinal fusion, includes an implant having an implant body. The device includes a graded radiopacity calibration tool integrated with the implant body. The tool has a plurality of graded levels of radiopacity representative of a range of bone density parameter amounts. Each of the graded levels corresponds to a different bone density parameter amount. A method is provided that uses the device to determine a degree of one of bone maturity, strength, osteoporotic state, state of healing and state of degrading bone tissue based on a comparison of a bone at the site in the image and radiopacity correlated from a calibration standardized curve defined by the standard, with a range of grey levels representative of degrees of one of the bone maturity, the strength, the osteoporotic state, the state of healing and the state of degrading bone tissue.

22 Claims, 8 Drawing Sheets

(56) References Cited

U.S. PATENT DOCUMENTS

| | | | |
|---|---|---|---|
| 7,815,682 | B1 | 10/2010 | Peterson et al. |
| 7,867,277 | B1 | 1/2011 | Tohmeh |
| 7,951,199 | B2 | 5/2011 | Miller |
| 8,105,382 | B2 | 1/2012 | Olmos et al. |
| 8,187,334 | B2 | 5/2012 | Curran et al. |
| 8,343,224 | B2 | 1/2013 | Lynn et al. |
| 8,690,949 | B2 | 4/2014 | Messerli et al. |
| 9,028,553 | B2 | 5/2015 | Lindenmann et al. |
| 9,700,425 | B1 | 7/2017 | Smith et al. |
| 9,730,802 | B1 | 8/2017 | Harvey |
| 9,980,780 | B2 * | 5/2018 | Lang .................. H05K 999/99 |
| 10,478,313 | B1 | 11/2019 | Sweeney, III |
| 10,485,897 | B2 * | 11/2019 | Erbe .................. A61L 27/46 |
| 2008/0177378 | A1 * | 7/2008 | Asgari ............... A61L 27/427 |
| | | | 623/1.38 |
| 2009/0105824 | A1 | 4/2009 | Jones et al. |
| 2012/0063568 | A1 | 3/2012 | Lang et al. |
| 2012/0292814 | A1 | 11/2012 | Spratt et al. |

OTHER PUBLICATIONS

Suman, SK et al. Development of Highly Radiopaque Flexible Polymer Composites for X-ray Imaging Applications and Copolymer Architecture-Morphology-Property Correlations, European Polymer Journal, V. 95, Oct. 2017, p. 41-55.

Walsh, WR, Pelletier, MH, Bertollo, N, Christou, C, Tan, C. Does Peek/HA Enhance Bone Formation Compared With Peek in a Sheep Cervical Fusion Model? Clinical Orthopaedics and Related Research. 2016;474(11):2364-2372. DOI:10.1007/S11999-016-4994-X.

Grigorian, EA, Druzhinin, VN, Kolesov, VG. [A Method of Calibrating the Aluminum Wedge for X-ray Photometric Research in Occupational Pathology].[Article in Russian] GIG TR Prof Zabol. <https://www.ncbi.nlm.nih.gov/pubmed/2591813> 1989;(10):45-7.

M.B. Kinds, L.W. Bartels, A.C.A. Marijnissen, K.L. Vincken, M.A. Viergever, F.P.J.G. Lafeber, H.W.A. M. De Jong, Feasibility of Bone Density Evaluation Using Plain Digital Radiography, in Osteoarthritis and Cartilage, vol. 19, Issue 11, 2011, pp. 1343-1348, ISSN 10634584, https://doi.org/10.1016/j.joca.2011.08.003.

Dundar, Nesrin; Guneri, Pelin; Onem, Erinçand Boyacioglu, Hayal. Construction of a Copper Stepwedge With Aluminum Equivalent Mean Gray Values. J. Appl. Oral Sci. [Online], 2010, vol. 18, N.4, pp. 390-396. Available from: <http://www.scielo.br/scielo.php?script=sci_arttext&pid=S1678-77572010000400012&Ing=en&nrm=iso>. ISSN 1678-7757. http://dx.doi.org/10.1590/S1678-77572010000400012.

J.G. Skedros, A.N. Knight, T.C. Pitts, P.J. O'Rourke, W.Z. Burkhead, Radiographic Morphometry and Densitometry Predict Strength of Cadaveric Proximal Humeri More Reliably Than Age and DXA Scan Density, J Orthop Res 34(2) (2016) 331-41.

R.B. Martin, T. Papamichos, G.A. Dannucci, Linear Calibration of Radiographic Mineral Density Using Video-Digitizing Methods, Calcif. Tissue Int. 47 (1990) 82-91.

"Aluminum Step Wedge," Copyright 2009 by Margraf Dental MFG. Inc., <http://www.margrafdental.com/aluminum-step-wedges.html>.

* cited by examiner

IMPLANT WITH GRADED RADIOPACITY CALIBRATION FEATURE

FIELD

The present technology is generally related to an implant device with a graded radiopacity calibration tool or feature.

BACKGROUND

Surgeons would benefit from an improved means for assessing fusion or union in patients over time as healing progresses. In the spine, when bone is encouraged to grow between two vertebral bodies, to create one biomechanically integrated unit, it is called spinal fusion. Fusion is typically achieved using implants made of metal, plastic or composite materials placed between adjacent vertebral bodies; additional implants, also made of metal or other materials to eliminate motion (called stabilization) and then biologic materials (including a variety of bone grafts) to create a biological scaffold, and to encourage bony growth between the vertebrae. In orthopaedic trauma, a similar need exists in assessing the maturity of a fracture callus.

Clinically, achieving fusion is important, because it represents a time in which patients may reasonably return to the more challenging activities of their work or daily life without expecting adverse consequences. Yet the confirmation that fusion has been achieved is problematic. The achievement of fusion may in some cases also be a point of contention in medical litigation, but two experts may reasonably differ on interpretation of fusion status in an uncalibrated film. In clinical research studies, fusion is often an endpoint of the study, but the skill of an investigator in reading fusion status from a series of x-rays or CT scans can be a source of inaccuracy or bias in the study.

Researchers have used "step wedges" made of aluminum of different thicknesses, to provide a calibration scale that can be used with contact radiographs to assess bone mineral density. Such wedges can still be obtained for dental use (margrafdental.com/aluminum-step-wedges), or may be custom machined for use in evaluating bone mineral content/mineral density in whole bones. [Suman, S K et al. Development of highly radiopaque flexible polymer composites for X-ray imaging applications and copolymer architecture-morphology-property correlations, European Polymer Journal, V. 95, October 2017, P. 41-55, incorporated herein by reference in full.] The density of bone is often described in millimeters of aluminum thickness, but may also be converted to an equivalent mineral content of bone or bone density by correlating to tissues of known density. Variants of the aluminum step wedge have been made by embedment or creation of different concentrations of radiopaque solution [Walsh W R, Pelletier M H, Bertollo N, Christou C, and Tan C. Does PEEK/HA Enhance Bone Formation Compared With PEEK in a Sheep Cervical Fusion Model? *Clinical Orthopaedics and Related Research.* 2016; 474(11):2364-2372. doi:10.1007/s11999-016-4994-x. Gig Tr Prof Zabol. 1989; (10):45-7, incorporated herein by reference in full.] Such a "composite material" calibration wedge can include a radiolucent polymer, and a radiopaque filler containing, for example a calcium compound or other inorganic material. A solution containing an inorganic suspension (e.g. Barium sulfate) may also be introduced to a triangular-shaped vessel to create a calibration wedge.

The calibration scale typically allows researchers to convert image grey levels from an x-ray or other radiographic image to a relevant measure of bone density or bone mineral content (BMC), in order to provide a calibrated, quantitative measure of the bone density or BMC.

A typical problem facing one that must interpret such images, however, is that variations in the X-ray parameters, as well as the variety of tissue thickness in the patient make it difficult to properly adjust the image so that a calibrated measure of grey level value may be obtained.

SUMMARY

The techniques of this disclosure generally relate to utilizing an implant to place a calibration tool or feature inside the body (beneath the tissues) and then using the feature to assess the maturity of a developing fusion mass or callus. Such an implant may further have an orientation feature, to assist in confirming a radiographic view that offers the opportunity to employ the calibration feature.

The integrated calibration tool or feature is configured to capture a degree of bone maturity, strength, osteoporotic state, or other features of healing or degrading bone tissue, in response to radiographic imaging radiating a graylevel scale of the tool or feature.

In one aspect, the present disclosure provides an implant device for use in achieving spinal fusion that includes an implant having an implant body. The device includes a graded radiopacity calibration tool integrated with the implant body. The tool has a plurality of graded levels of radiopacity representative of a range of bone density parameter amounts. Each of the graded levels corresponds to a different bone density parameter amount.

The disclosure provides a method of using such an implant feature to calibrate a radiographically-obtained image, whether in film or digital format.

Another aspect of the disclosure includes a method of measuring an implant fusion. The method includes capturing, in response to ionizing radiation generated by an imaging machine, an image of a fusion implant device at an implant site comprising a graded radiopacity calibration tool having a plurality of graded levels of radiopacity representative of a range of bone density parameter amounts. Each of the graded levels corresponds to a corresponding different one bone density parameter amount. The method includes detecting, by a processor, a region of interest in the image. The region of interest includes the fusion implant device and the plurality of graded levels of radiopacity in the image. The plurality of graded levels of radiopacity in the image is configured to represent a grey level scale from white to black or dark grey.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting.

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other. Generally, similar spatial references of different aspects or components indicate similar spatial orientation and/or positioning, i.e., that each "first end" is situated on or directed towards the same end of the device. Further, the use of various spatial terminology herein should not be interpreted to limit the various location techniques or orientations for identifying objects or machines. In the discussion below, the term 'fusion' is intended to have a broad meaning, encompassing union of long bones, as well as conversion of a joint into a solid arthrodesis, whether in the spine, or another joint of the appendicular skeleton.

Patients have different capacities to heal, based upon age, prior medical history, comorbidities, the difficulties of the surgical site and other factors. As a consequence, surgeons cannot easily predict when fusion would occur in a given patient. Yet the technical objective is fusion, and the time when the patient achieves fusion is relevant to patient care and resumption of activities of daily living, etc.

Fusion is typically assessed radiographically, yet the available methods are limited in certain respects. Surgeons can take simple, plain film or digital X-rays or radiographs, and look for image patterns on the X-ray that are thought to correlate with fusion. Yet these frequently are unclear such that fusion status cannot be as accurately assessed. Radiopaque implants, as well as overlapping bony features can hide limitations in fusion mass due to projection effect errors. Surgeons can take flexion-extension films using radiography, in which the patient is asked to bend forward and backward, and measure the position of sequential vertebrae to assess relative motion at the target level, but these are often unclear. Another possibility is to take computed tomographic (CT) scans at fine resolution. CT scans have the advantage of providing the clearest image of the fusion site, but have the disadvantage of exposing the patient to a high dose of irradiation that is much greater than that of the traditional X-ray. CT scans also require specialized equipment, which may not be accessible or cost effective. As a result, they cannot be used routinely, and are usually reserved for situations in which healing is in doubt.

Added to these limitations are projection effect issues from radiodense implant materials (metallic implants and calcium-based grafting materials, as well as mineralized bone grafts are common), in which a dense material can obscure the fusion site, making it difficult to determine whether fusion has occurred. Additionally, patients have varying degrees of intervening body fat and muscle, with some morbidly obese patients having extensive tissue penetration requirements in order to form a usable x-ray. This makes imaging more inconsistent from patient to patient, and adds to the challenge of assessing bone maturity, strength, osteoporotic state, or other features of healing or degrading bone tissue.

The embodiments herein integrate a graded radiopacity calibration tool or feature into an implant device where the calibration tool is placed near the fusion site in the normal course of surgery by virtue of the implantation of the implant device. The calibration tool may be integrated, for example, into intervertebral implant, a rod, a cross-brace, and a corpectomy device. Other possibilities also exist, and this list is not intended to be complete.

The implant devices of FIGS. 1-5A may include a spinal fusion implant device such as a fusion interbody device. Thus, only the implant device 100 of FIG. 1 will be described in detail. The implant device may be used in humans, but also in non-human mammals such as dogs or cats, non-human reptiles, birds, fish and amphibians.

Figure 1:
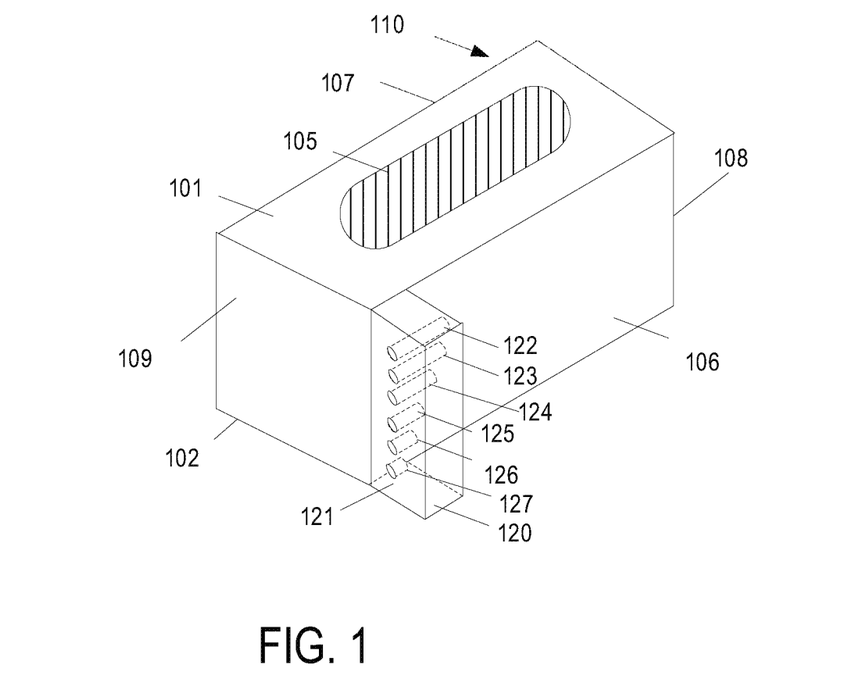
FIG. 1 is a perspective view that illustrates implant device with an integrated graded radiopacity calibration tool.

FIG. 1 is a perspective view that illustrates implant device 100 with an integrated graded radiopacity calibration tool 120. The implant device 100 may include a top surface 101, a bottom surface 102 and four side surfaces 106, 107, 108 and 109. The implant device 100 may have a generally rectangular or box shape. Alternatively, the implant may be generally oval or cylindrical shape circular, D-shaped, U-shaped, or form a myriad of shapes as required by the procedure and the subject patient's anatomy. The surfaces of the implant device may be smooth or textured, surface-treated, and may include ridges or various forms of teeth.

The implant device 100 may include an aperture 105 that extends from the top surface 101 down to and through the bottom surface 103. Optionally, the side walls 108, 106, 109, 110 may have communicating perforations or openings. In the illustration the aperture 105 is shown as oblong. However, the geometric shape of the aperture 105 may have other geometric shapes, such as without limitation, circular, oval, square, and rectangular. The aperture 105 may be filled with a material to promote fusion between adjacent bony structures or vertebrae. The top surface 101, bottom surface 102 and four side surfaces 106, 107, 108 and 109 and aperture 105 form the medical implant 110 or medical implant body.

The integrated graded radiopacity calibration tool 120 may include an appendage 121 extending from a respective side of the implant 110. The appendage 121 may include graded radiopaque markers 122, 123, 124, 125, 126 and 127, for example.

Each graded radiopaque marker 122, 123, 124, 125, 126 and 127 is a corresponding different level of radiopacity to differentiate a range of bone mineral density (BMC). The grading of the graded radiopaque markers is based on at least one dimension of the marker geometric shape. In the illustration, at least one dimension of the graded radiopaque marker is a length of a graded radiopaque marker. The graded radiopaque marker 127 with the smallest length may correspond to a level of radiopacity configured to be only slightly more radiopaque than background density on the film. The graded radiopaque marker 122 with the largest or longest length may correspond to a level of radiopacity configured to exceed the radiopacity range of BMC. Thus, the graded radiopacity tool 120 provides a radiopacity graded visual indicator representative of a radiopacity range upon imaging directly at the implantation site. As can be appreciated, bones in an image, such as an X-ray image may appear white or light grey. On the other hand, muscle and skin may appear black or dark grey. Accordingly, the smallest radiopacity graded step, level or marker may appear dark grey. On the other hand, the largest radiopacity graded step may appear white. Thus, one graded level may be radiolucent to appear dark grey. The graded levels of radiopacity are arranged in a grey level, such that each level is incrementally darker or lighter than the next. In a digital or film x-ray or CT scan, a clinician can assess the state of the fusion mass, according to how radiopaque it is relative to the range of the calibration markers as a scale. The calibration feature, after its use in calibrating the image, can permit the clinician to interpret the fusion mass in terms of bone mineral density, calibrated houndsfield units, gray level, a fusion maturity scale, fusion status or millimeters of calibrated metal equivalents. This assessment of fusion/fusion mass via calibrated imaging for bone density enables both quantitative comparison of pre- and post-op imaging and long-term bony maturation, but also standardizes radiographic fusion assessment which ultimately allows for better comparison across treatment methods and patient populations.

In general, a smallest graded level of radiopacity is configured to appear slightly more than a background density or radiolucent in an image captured by ionizing radiation. The largest graded level of radiopacity is configured to appear as exceeding the range of the bone density parameter amounts. The graded levels between the smallest and the largest include intermediate levels of radiopacity of different levels of bone density parameters as such parameter would appear in an image captured by ionizing radiation.

The graded plurality of graded steps, levels or markers of radiopacity are configured to represent, in response to ionizing radiation, a degree of bone maturity, strength, osteoporotic state, or other features of healing or degrading bone tissue.

The graded radiopaque marker 122, 123, 124, 125, 126 and 127 may be formed in the appendage 121 by creating a cylindrical shape of a different length. Each graded radiopaque marker 122, 123, 124, 125, 126 and 127 may be stacked in equidistant increments below each level. The radiopaque markers may be made of biocompatible metallic material as described herein.

While the illustration only shows one aperture extending from the top surface 101 to and through the bottom surface 102, the device may have other apertures such as an aperture through side wall 106 to and through side wall 107 and/or an aperture through side wall 108 to and through side wall 109.

The calibration tool 120 of the implant device 100 is configured as graded thicknesses of a radiopaque material that may be used to assess bone maturity, strength, osteoporotic state, or other features of healing or degrading bone tissue. The appendage 121 may be made of materials being removed from different depths, such as by drilling or boring through the material of the appendage 121. The holes in the appendage may be filled to create the graded radiopacity being graded by graded density of composite filler in the appendage 121 of the implant device 100. The composite material may be any of boron nitride in polyether ether ketone (PEEK), Hydroxyapatite (HA) in PEEK, the SOLVAY® osteoconductive PEEK, composites of silicon nitride, and PEEK-HA by InVibio®. The filler of the composite may be barium sulfate, a calcium phosphate material, metallic wires or rods embedded to specific depths or other configurations. The calcium phosphate material may be configured as a composite material with a plastic, in some embodiments. The proportion of filler to plastic may have different densities or ratios to vary the degree of radiopacity in an image.

In some embodiments, the graded radiopacity steps, level or markers of the calibration tool may be made of a biocompatible metallic material, e.g., aluminum, titanium, molybdenum, cobalt chrome, tantalum, stainless steel, and their alloys. Alternative embodiments for a step or marker could be achieved with additive manufacturing techniques by creating a specified void to make an equivalent indicator within the implantable device.

For example, the holes, denoted by the markers 122-127, as shown in FIG. 1, are drilled to different depths in a uniform block depth for a radiopaque (e.g. metallic) implant. The depths of the machined surfaces, corresponding to the holes of markers 122-127, would create an implant material depth difference that would be interpreted on X-ray as different grey levels (or graylevels).

For a radiolucent implant (e.g. PEEK), the markers could be different lengths of one radiopaque material (e.g. a metallic wire, or a calcium phosphate bar), and could be configured as shown. As an example, a solution of calcium phosphate of varying densities may be used to form an injectable filler. The varying densities may form markers 122-127 of varying radiopacity.

For the sake of brevity, only the differences in the implant devices 200, 300, 400 and 500 of FIGS. 2-5A relative to the implant device 100 of FIG. 1 will be described in detail.

Figure 2:
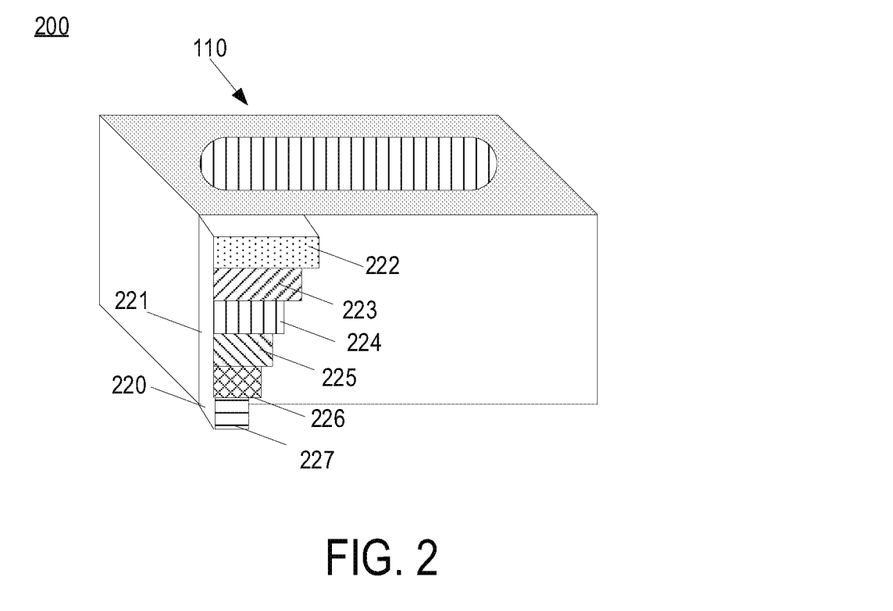
FIG. 2 is a perspective view that illustrates another implant device with an integrated graded radiopacity calibration tool.

FIG. 2 is a perspective view that illustrates another embodiment of an implant device 200 with an integrated graded radiopacity tool 220. The implant device 200 includes implant 110. The integrated graded radiopacity tool 220 may include an appendage 221 extending from a respective side of the implant 110. In the illustrations, the appendage 221 is configured as a step wedge shape. The appendage 221 may include a graded radiopaque markers 222, 223, 224, 225, 226 and 227, for example, arranged in a staircase.

Each graded radiopaque marker 222, 223, 224, 225, 226 and 227 being a corresponding different level of radiopacity to differentiate a range of bone mineral density (BMC). The grading of the graded radiopaque markers may be based on at least one dimension of the marker geometric shape. In the illustration, the at least one dimension of the graded radiopaque marker is a length of a graded radiopaque marker. The graded radiopaque marker 227 with the smallest length may correspond to a level of radiopacity configured to be only slightly more radiopaque than background density on the film. The graded radiopaque marker 222 with the largest or longest length may correspond to a level of radiopacity configured to exceed the radiopacity range of BMC. Thus, the graded radiopacity tool 220 provides a radiopacity graded visual indicator representative of a radiopacity range upon imaging.

The graded radiopaque marker 222 is a first step level and denoted with dotted hatching. The graded radiopaque marker 223 is a second step level and denoted with diagonal hatching in a first direction. The graded radiopaque marker 224 is a third step level and denoted with vertical hatching. The graded radiopaque marker 225 is a fourth step level and denoted with diagonal hatching in a second direction. The graded radiopaque marker 226 is a fifth step level and denoted with cross hatching. The graded radiopaque marker 227 is a sixth step level and denoted with horizontal hatching. Each step level may be made of or coated with material of varying radiopacity, or may use a single material and utilize the differences in length dimension to define the calibration scale.

The appendage 221 of the calibration tool 220 may be a machined or manufactured as "step wedge". The appendage 221 may be made of composite materials, graded by material thickness to create the "step wedge". By way of non-limiting example, the composite material may be one of boron nitrite in PEEK, Hydroxyapatite (HA) in PEEK, the SOLVAY® osteoconductive PEEK, composites of silicon nitride, and PEEK-HA by InVibio®. Such appendage 221 may also be made of a single material, e.g. titanium or its alloys, cobalt-chromium, tantalum, stainless steel, and the like. The material of steps 221 may be the same or different from that of the rest of implant 200.

By way of non-limiting example, each radiopaque marker may comprise a single material. However, the thickness of the material may vary, as the thickness varies the degree of radiopacity varies. Thus, each marker of different thickness may appear to have a different graylevel in the radiographically-produced image. The single material may be a metal that can be welded to form the step wedge.

In yet another example, the composition of material of a solution may be varied such that the markers when formed have varying degrees of radiopacity.

In some embodiments, the "step wedge" may be integrated into the body of the implant device 200 without the need for an appendage 221. For example, the implant device 200 may formed with a cavity for placement of the step wedge without the need for an appendage.

Figure 3:
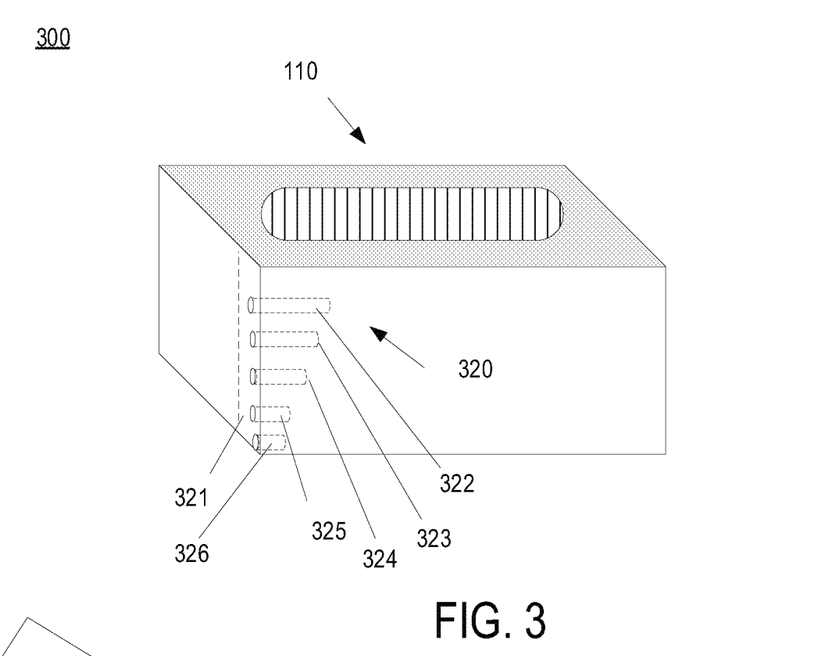
FIG. 3 is a perspective view that illustrates another implant device with an integrated graded radiopacity calibration tool.

FIG. 3 is a perspective view that illustrates another embodiment of an implant device 300 with an integrated graded radiopacity tool 320. The implant device 300 includes implant 110. The body 321 of the implant device 300 may include graded radiopaque markers 322, 323, 324, 325, and 326, for example, integrated and formed within the body 321 without the need for an appendage. The form factor of the implant device 300 does not require alteration to integrate the integrated graded radiopacity tool 320. The graded radiopaque markers 322, 323, 324, 325, and 326 are essentially the same as the graded radiopaque markers 122, 123, 124, 125, and 126 described in relation to FIG. 1. The embodiment of FIG. 3 includes less levels of radiopacity markers. Accordingly, the tools described herein may include any number of levels greater than 1.

In an embodiments, where the tool 320 is integrated into the form factor of the implant device, the form factor may be formed from at least one material with continuously changing degrees of radiopacity to provide a continuously changing radiopacity grey level scale.

Figure 4:
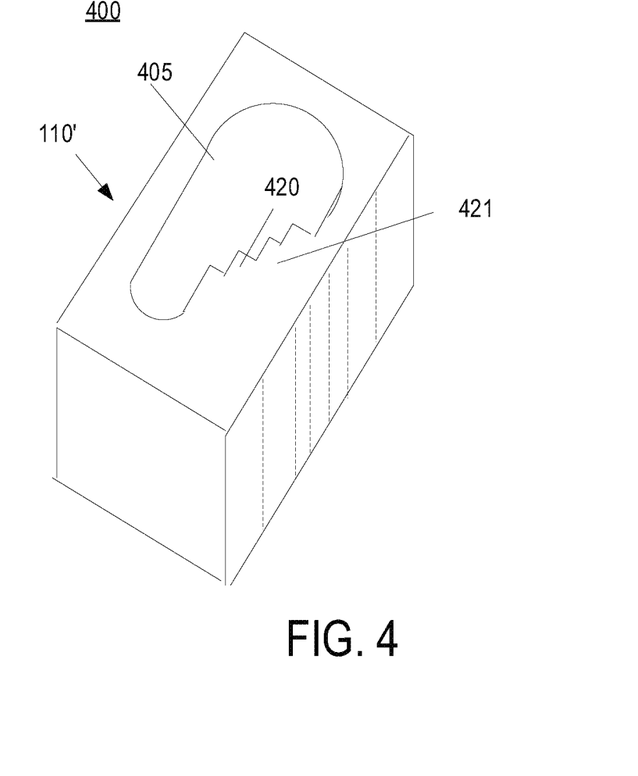
FIG. 4 is a perspective view that illustrates yet another implant device with an integrated graded radiopacity tool.

FIG. 4 is a perspective view that illustrates yet another embodiment of an implant device 400 with an integrated graded radiopacity tool 420. The implant device 300 includes implant 110' and aperture 405. The implants 110 and 110' differ from each other because of the apertures 105 and 405. The integrated graded radiopacity tool 420 may include an appendage 421 extending from a respective side of the implant 110' into the aperture 405. The appendage 421 is configured as a step wedge shape. The appendage 421 may include graded radiopaque markers similar to markers 222, 223, 224, and 225, for example, arranged in a staircase.

Figure 5A:
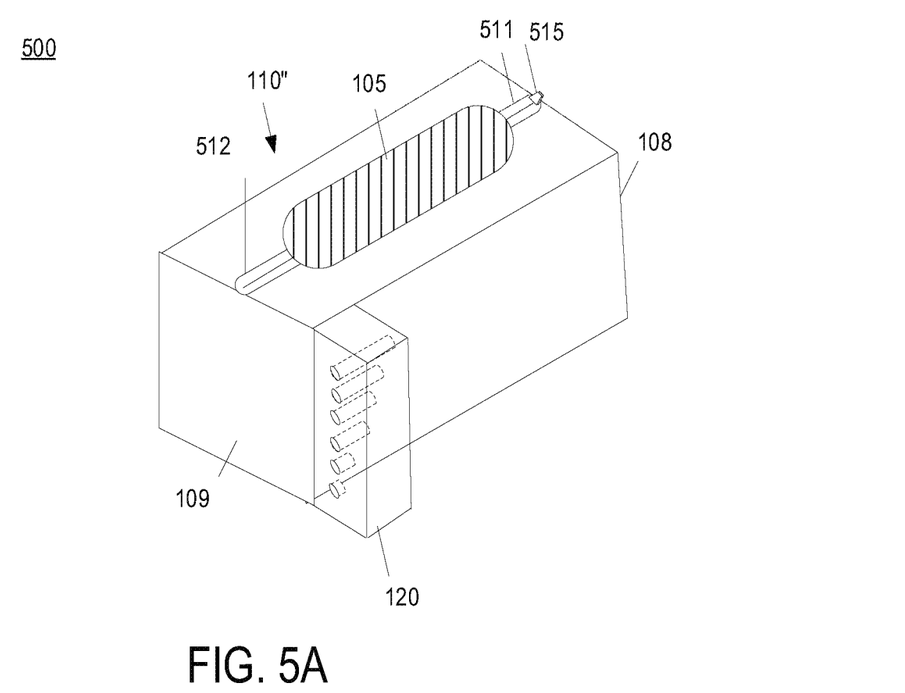
FIG. 5A-5B are a perspective view and end view that illustrate yet another implant device with an integrated graded radiopacity tool.
Figure 5B:
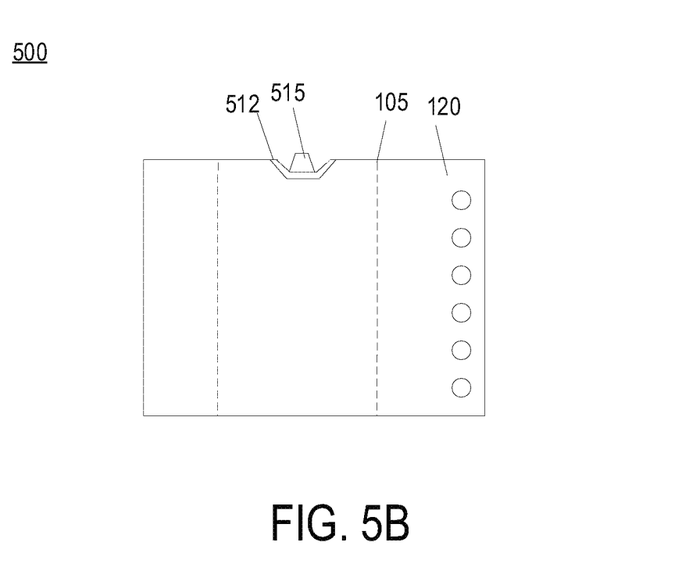

FIG. 5A-5B are a perspective view and end view that illustrate yet another embodiment of an implant device 500 with an integrated graded radiopacity tool 120, as shown in FIG. 1. The implant device 500 includes implant 110" that is generally similar to the implant 110. The difference is that the top surface include channel 512 and blade 511 that extend from side walls 108 and 109, respectively to the aperture 105. Features 511 and 512 allow an appropriate image alignment to minimize artifact from malalignment and projection effect. The features 511 and 512 could be substituted with other features that might be used to align the implant, including differently sized circular portals, etc. In FIG. 5B, the dashed line represents the aperture though the body of implant 100". The orientation guide 515 may be configured to denote an image plane for image calibration, in response to ionizing radiation.

Figure 6A:
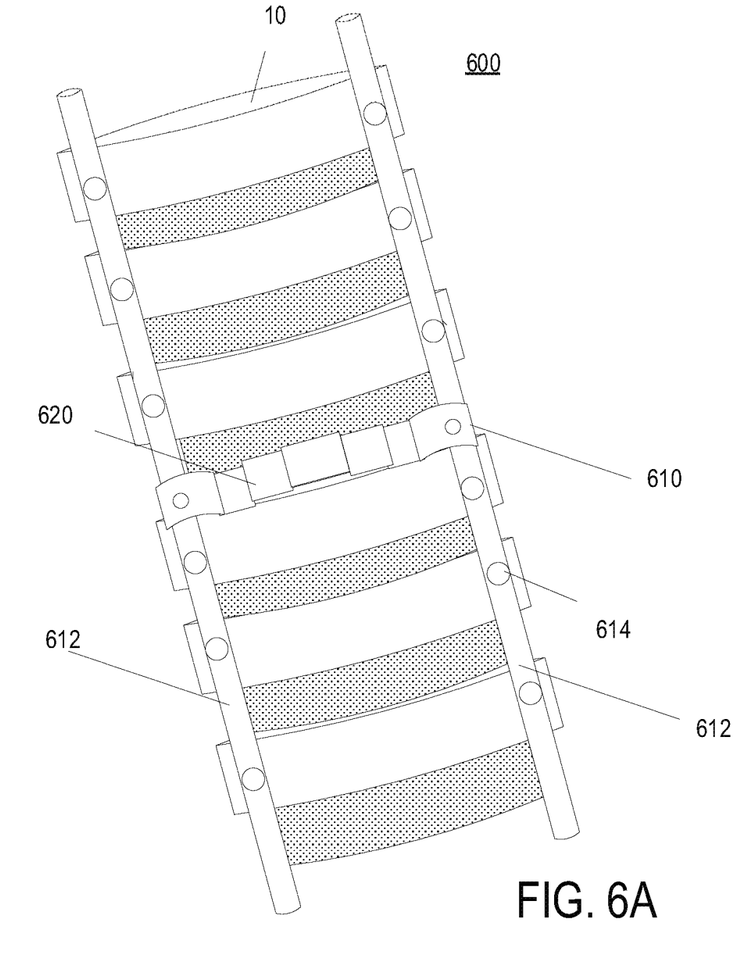
FIG. 6A is a perspective view that illustrates yet another implant device with the graded radiopacity tool configured to be attached to a vertebrae.

FIG. 6A is a perspective view that illustrates yet another embodiment of an implant device 600 with the graded radiopacity tool 620 configured to be attached to a vertebrae 10 of a patient. The implant device 600 is a system, such as SOLERA, by Medtronic, Inc. that includes rods 612 and pedicle screws 614 and at least one cross brace 610. The cross brace 610 may be configured to be affixed to a subject via screws to the rod. The cross brace 610 stabilizes the rods 612. The rods 612 are shown extending along several levels (i.e., vertebrae 10) in the spine.

Figure 6B:
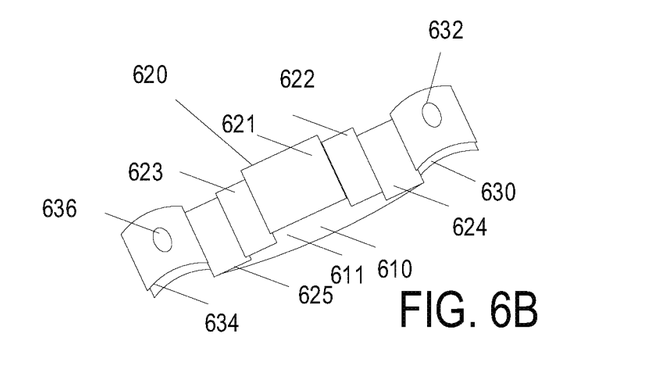
FIG. 6B is a perspective view of the graded radiopacity tool of FIG. 6A.

FIG. 6B is a perspective view of an embodiment of a graded radiopacity tool 620 of FIG. 6A. The graded radiopacity tool 620 is incorporated into a cross-brace 610. The graded radiopacity tool 620 is integrated into the cross-brace 610 and may include a plurality of steps or levels 621, 622, 623, 624, and 625. The plurality of steps or levels 621, 622, 623, 624, and 625 are graded radiopaque markers. In the illustration, the step or level 621 can be flanked by attachment sites levels 622 and 623 which serve to attach the cross-brace 610 to the rest of the construct, such as rods 612, as shown in FIG. 6A. The steps or levels 622 and 623 may have the same level. The step or level 624 can be flanked by fastener 630 of the cross-brace 610 and step 622. Step or level 625 is flanked by fastener 634 of the cross-brace 610 and step or level 623. The fasteners 630 and 634 may include apertures 632 and 636 for receiving a screw to fasten the cross-brace 610 with the graded radiopacity tool 620 to rods 612. The cross-brace 610 may include a cross-brace strap 611 above which is the graded radiopacity tool 620.

In this embodiment, the steps or levels 621, 622 and 624 form a first staircase where step or level 624 may be the lowest level of the first staircase. The steps 621, 623 and 625 form a second staircase where step or level 625 may be the lowest level of the second staircase. The first staircase and the second staircase can share the same upper step or level 621.

The graded radiopaque markers 621, 622 and 624 can be of a first staircase being a corresponding different level of radiopacity to differentiate a range of bone mineral density (BMC). The graded radiopaque markers 621, 623 and 625 can be of a second staircase being a corresponding different level of radiopacity to differentiate a range of bone mineral density (BMC), however, levels 622 and 623 may have the same level of radiopacity. The levels 624 and 625 may have the same level of radiopacity. In some embodiments, in lieu of two staircases, a single staircase of radiopacity levels may be used to form a wedge shape.

Figure 7A:
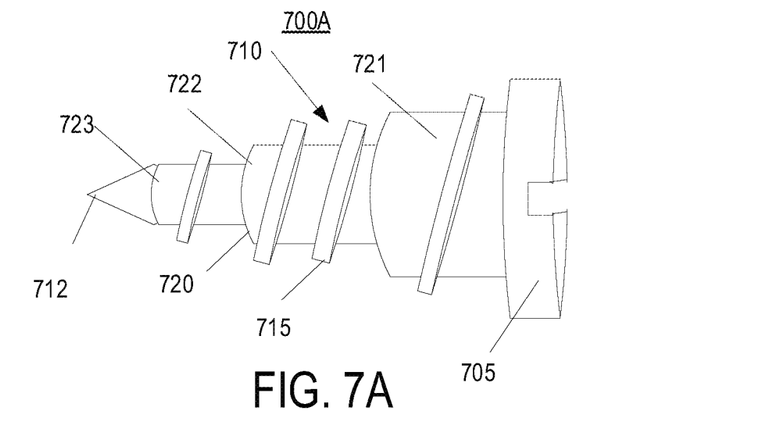
FIG. 7A is a perspective view that illustrates yet another implant device with an integrated graded radiopacity component in a screw.

FIG. 7A is a perspective view that illustrates yet another embodiment of an implant device 700 with an integrated graded radiopacity tool 720. The implant device 700 includes a surgical screw with a head 705 and a screw shaft 710 with threads 715. The screw shaft 710 has one end attached to the head and a second end tapering to a point 712. The screw shaft 710 has integrated into its length the graded radiopacity tool 720.

The screw shaft 710 or shank has a graded configuration. The tool 720 includes a first screw shaft portion 721 having a first diameter. The first screw shaft portion 721 is adjacent the head 705. The tool 720 includes a second screw shaft portion 722 adjacent to the first screw shaft portion 721. The second screw shaft portion 722 has a second diameter smaller than the first diameter. The tool 720 includes a third screw shaft portion 723 which is adjacent to the second screw shaft portion 722. The third screw shaft portion 723 has a third diameter smaller than the second diameter.

Each screw shaft portion 721, 722, and 723 can correspond to a different level of radiopacity to differentiate a range of bone mineral density (BMC). The grading of the screw shaft portion can be graded based on at least one dimension. In the illustration, the at least one dimension of the screw shaft portion a diameter of a screw shaft portion. The screw shaft portion 723 with the smallest diameter may correspond to a level of radiopacity configured to be only slightly more radiopaque than background density on the film. The screw shaft portion 721 with the largest diameter may correspond to a level of radiopacity configured to exceed the radiopacity range of BMC. Thus, the graded radiopacity tool 720 provides a radiopacity graded visual indicator representative of a radiopacity range upon imaging.

The at least one dimension of the screw shaft portion may include a length of the portion where the length of each screw shaft portion may be reduced, as well.

Figure 7B:
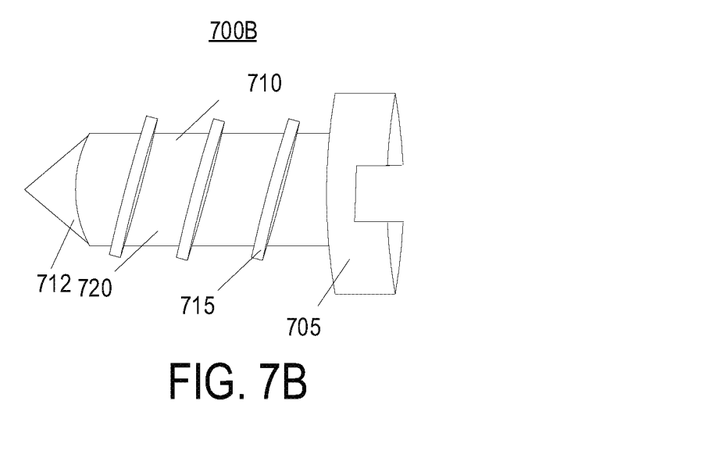
FIG. 7B is a perspective view that illustrates yet another implant device with an integrated graded radiopacity component in a screw.

FIG. 7B is a perspective view that illustrates yet another implant device with an integrated graded radiopacity component in a screw 700B. A standard medical screw configuration may be used as a self-calibrating object so long as it is an object of known dimensions and processed with a contemporary imaging system, such as without limitation an O-ARM™ Surgical Imaging System 2.0, by Medtronic Inc. The screw 700B may include a screw shaft 710 and threads 715. In some embodiments the integrated graded radiopacity tool 720 may be integrated into the shaft. For example, different levels of radiopacity may be used between threads 715.

Figure 8:
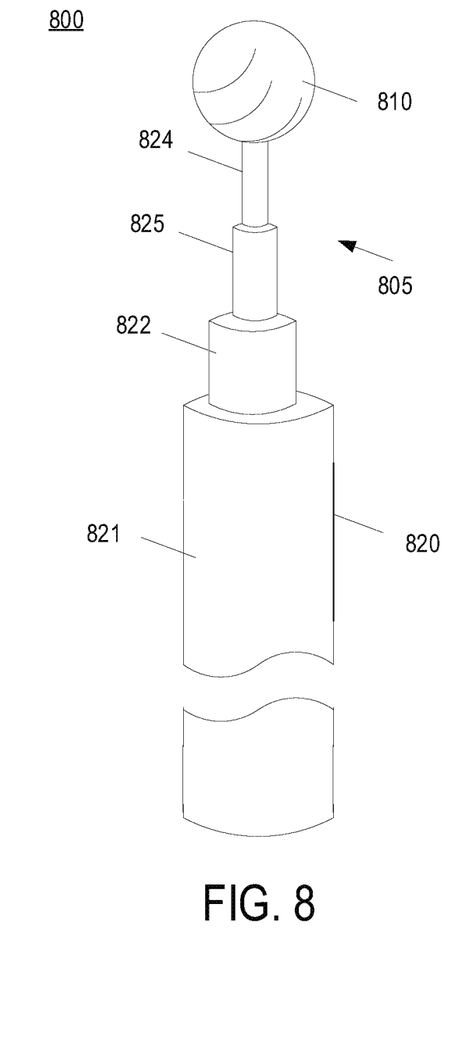
FIG. 8 is a perspective view that illustrates another implant device with an integrated graded radiopacity feature.

FIG. 8 is a perspective view that illustrates another embodiment of an implant device 800 with an integrated graded radiopacity tool 820. The implant device 800 of this embodiment can be used as a stabilization rod. The stabilization rod includes a graded rod body configuration. The implant device 800 includes a rod body 805 where the rod body is constructed and arranged as the integrated graded radiopacity tool 820

The tool 820 includes a first rod body portion 821 having a first diameter. The rod body 821 may be of any length appropriate to the surgical objective, and the remaining features 810, 824, 825, 822 may include the termination of the rod. The tool 820 includes a second rod body portion 822 having a second diameter smaller than the first diameter. The second rod body portion 822 is adjacent to the first rod body portion 821. The tool 820 includes a third rod body portion 823 having a third diameter smaller than the second diameter. The third rod body portion 823 is adjacent to the second rod body portion 822. The tool 820 includes a fourth rod body portion 824 having a fourth diameter smaller than the third diameter. The fourth rod body portion 824 is adjacent to the third rod body portion 823.

Each rod body portion 821, 822, 823 and 824 being a corresponding different level of radiopacity to differentiate a range of bone mineral density (BMD) or Bone mineral content (BMC). The grading of the rod body portion can be graded based on at least one dimension. In the illustration, the at least one dimension of the rod body portion a diameter of a rod body portion. The rod body portion 824 with the smallest diameter may correspond to a level of radiopacity configured to be only slightly more radiopaque than background density on the film. The rod body portion 821 with the largest diameter may correspond to a level of radiopacity configured to exceed the radiopacity range of the BMC. Thus, the graded radiopacity tool 820 provides a radiopacity graded visual indicator representative of a radiopacity range upon imaging.

The at least one dimension of the rod body portion may include a length of the portion where the length of each screw shaft portion may correspond to a different length, as well.

The implant device 800 may include a ball or head 810 at one end of the rod body 805. For example, the ball 810 can be positioned at one end of the fourth rod body portion 824. In the illustration, the first rod body is farthest from the ball or head 810 and corresponds to a radiopacity that may exceed the radiopacity range of the BMC.

The calibration tool may be an intrinsic feature of the implant (e.g., a variant implant wall thickness encompassing the internal graft), as shown in FIG. 4, in steps, as shown in FIG. 2, or continuous gradation; increasing screw diameters along the taper of the screw implant, as shown in FIG. 7A, or it may be a purpose-built feature that is machined or manufactured into the implant, as shown in FIGS. 2-4. In a continuous gradation, a triangular prism shape may be formed from high to low with a continuous change in grey levels.

The integrated graded radiopacity tool 120, 220, 320, 420, 520, 620, 720 and 820 can have at least one graded level of radiopacity. The integrated graded radiopacity tool 120, 220, 320, 420, 520, 620, 720 and 820 may be a single step configuration, corresponding to a minimal density required to establish that fusion has occurred. The single step configuration then becomes a yes/no test, similar to a pregnancy test in decisiveness.

The integrated graded radiopacity tool 120, 220, 320, 420, 520, 620, 720 and 820 can have two or more graded levels of radiopacity, with each level corresponding to a meaningful range of bone mineral density (BMC). The thinnest level will be only slightly more than background density on the film, and the most thick will exceed the range of BMC or bone density, thus providing a range.

The graded radiopacity tool may be used for assessing the maturity of a fusion mass in the spine, a developing union in a long bone fracture, or assessing osteoporosis at one or more clinically relevant sites.

The graded levels of radiopacity can be achieved by adding or subtracting radiopaque material (metallic, or non-metallic composite materials, typically) at each step, corresponding to a greater or lesser image grey level intensity on the final image. Such graded radiopaque amounts can be achieved by machining, additive manufacturing methods, creating a filler density gradient in a composite material, or by creating porosity in a composite material corresponding to each gradation. Materials envisioned include biocompatible metallic materials (e.g., aluminum, titanium, molybdenum, cobalt chromium, stainless steel, tantalum, and their alloys, etc.), non-metallic opaque materials (hydroxyapatite, TCP, etc.), and filled composite materials (e.g., boron nitrite in PEEK, Hydroxyapatite in PEEK, the SOLVAY® osteoconductive PEEK, composites of silicon nitride, PEEK-HA by InVibio®).

For instance, density is impacted by porosity/total pore volume and thus can be used as a method for creating graded levels. However, porosity/patterned porosity itself is also relevant to bony structure, such as trabecular structure. The density of the porous material, that is, the proportion of void space to solid space, can be varied to provide a calibration standard. Any radiopaque material, such as calcium based inorganic materials, porous metals, etc., may be used to create a graded series of steps by varying the amount of porosity at each step.

The implant containing the calibration tool may be used in a method to calibrate images of the implant and the bone density or BMC associated with interbody fusions, posterolateral fusion, facet fusions, and other spinal fusions. As described herein the term bone density parameter includes both bone density, bone mass and BMC.

The blocks of the methods described herein may be performed in the order shown or a different order. One or more of the blocks may be performed contemporaneously. One or more blocks may be added or omitted.

Figure 9:
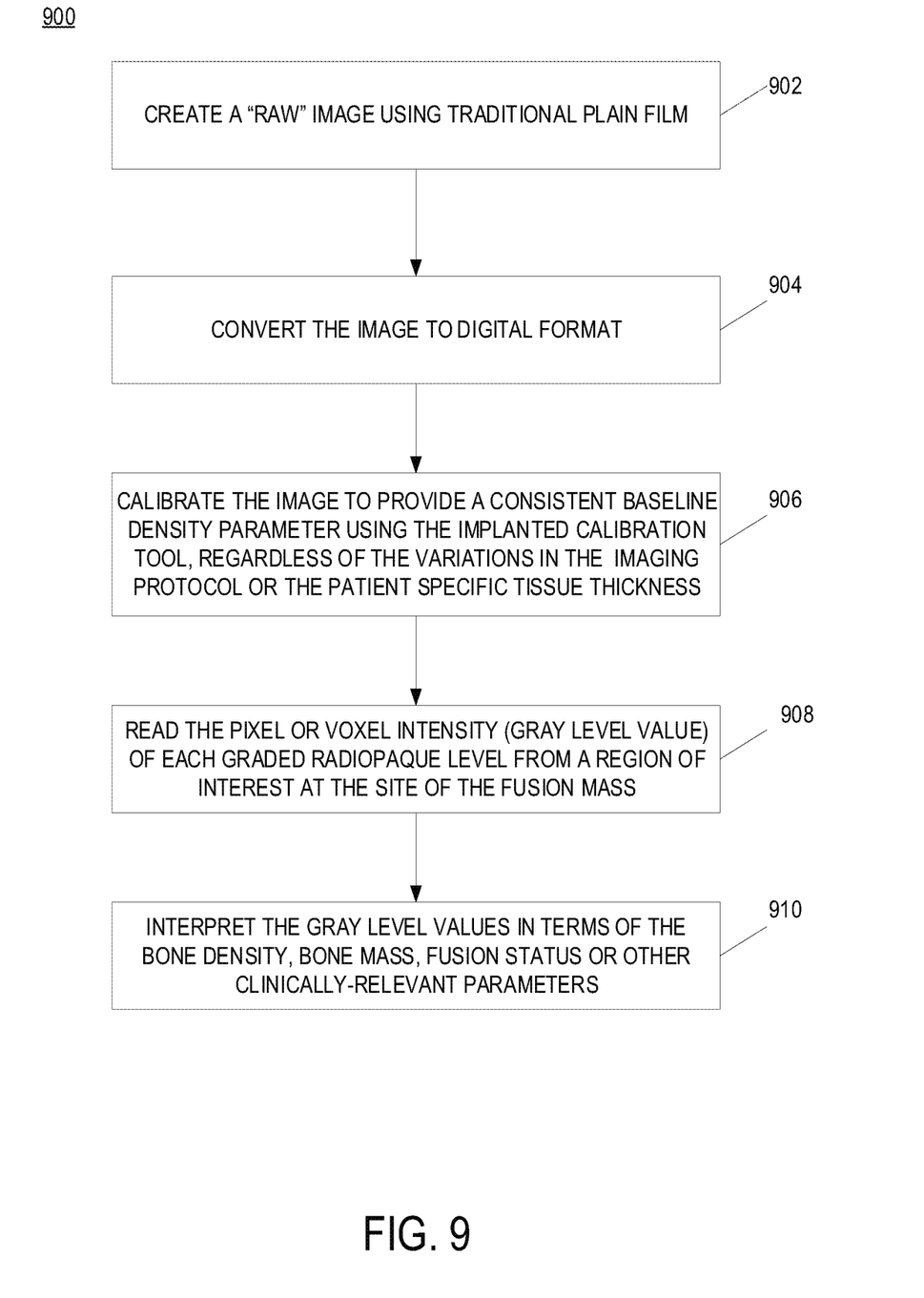
FIG. 9 is a flowchart of a method to calibrate images of a fusion site.

FIG. 9 is a flowchart of an embodiment of a method 900 to calibrate clinical images of a fusion site having anyone of the implant devices of FIGS. 1-4, 5A-5B, 6A-6B and 7-8. The method 900 may include, at block 902, creating a "raw" image using traditional plain film, digital X-ray, DEXA, or CT scanning technology. The "raw" image may include three-dimensional image that are reconstructed radiographic images from CT scans. The image may be a radiograph that may be a traditional film radiograph assessed by densitometry. The image may be a traditional film radiograph that is scanned and converted to digital format before calibration and assessment. The image may be captured digitally from the radiographic equipment. The imaging system may include an O-ARM™ Surgical Imaging System 2.0, by Medtronic Inc. Intraoperative, or free-standing CT scanners, fluoroscopes, dental X-ray systems, plain film or digital X-ray systems are among the types of imaging equipment that may be used to provide the image for calibration. The method 900 may include, at block 904, converting the "raw" image to a digital format, if required.

The method 900 may include, at block 906, calibrating the image to provide a consistent baseline density or baseline bone density parameter using the implanted calibration tool, regardless of the variations in the X-ray imaging or the patient specific tissue thickness. The method 900 may include, at block 908, reading the pixel or voxel intensity (grey level value) from a region of interest at the site of the fusion mass. The region of interest may be determined using feature extraction algorithms known in the art. The region of interest may correspond to the implant device with the integrated calibration tool. By way of non-limiting example, the feature extraction techniques may rely on stored data associated with the implant device type, size and shape to extract the implant device from the image data. In one or more embodiments, the feature extraction techniques may use feature extraction techniques to locate the radiopaque material, such as by the known radiopaque material composition. The radiopaque material composition may have a material signature or fingerprint within the image via a collection of identified pixels or voxels. The method 900 may include, at block 910, interpreting the grey level values of the graded radiopaque levels of the tool in terms of one or more of the bone parameter, a bone density, a bone mass, a fusion status or other clinically-relevant parameters based on the radiopacity of the calibration tool. The interpretation is a determination of the degree of bone maturity, strength, osteoporotic state, or other features of healing or degrading bone tissue based on a comparison of a bone at the site in the image and any one graded level of radiopacity correlated to a range of grey levels of a standardized calibration curve representative of degrees of one of bone maturity, strength, osteoporotic state, state of healing and state of degrading bone tissue. Anyone using the standardized calibration curve, whether manually, by measuring optical density, or by digital means (i.e., feature extraction), would compare the image results of the calibration tool to the standardized calibration curve defined by the standards. Either digitally, optically, or visually by a doctor, the degree of the equivalent bone density, or other parameters may be determined. In some embodiments, a different standardized calibration curve may be used for each different bone parameter to be evaluated. The standardized calibration curve for each bone parameter may be digitally stored so that pixels or voxels of the image of the feature or tool may be compared to a digital representation of the range of the grey levels of the calibration curve.

Figure 10:
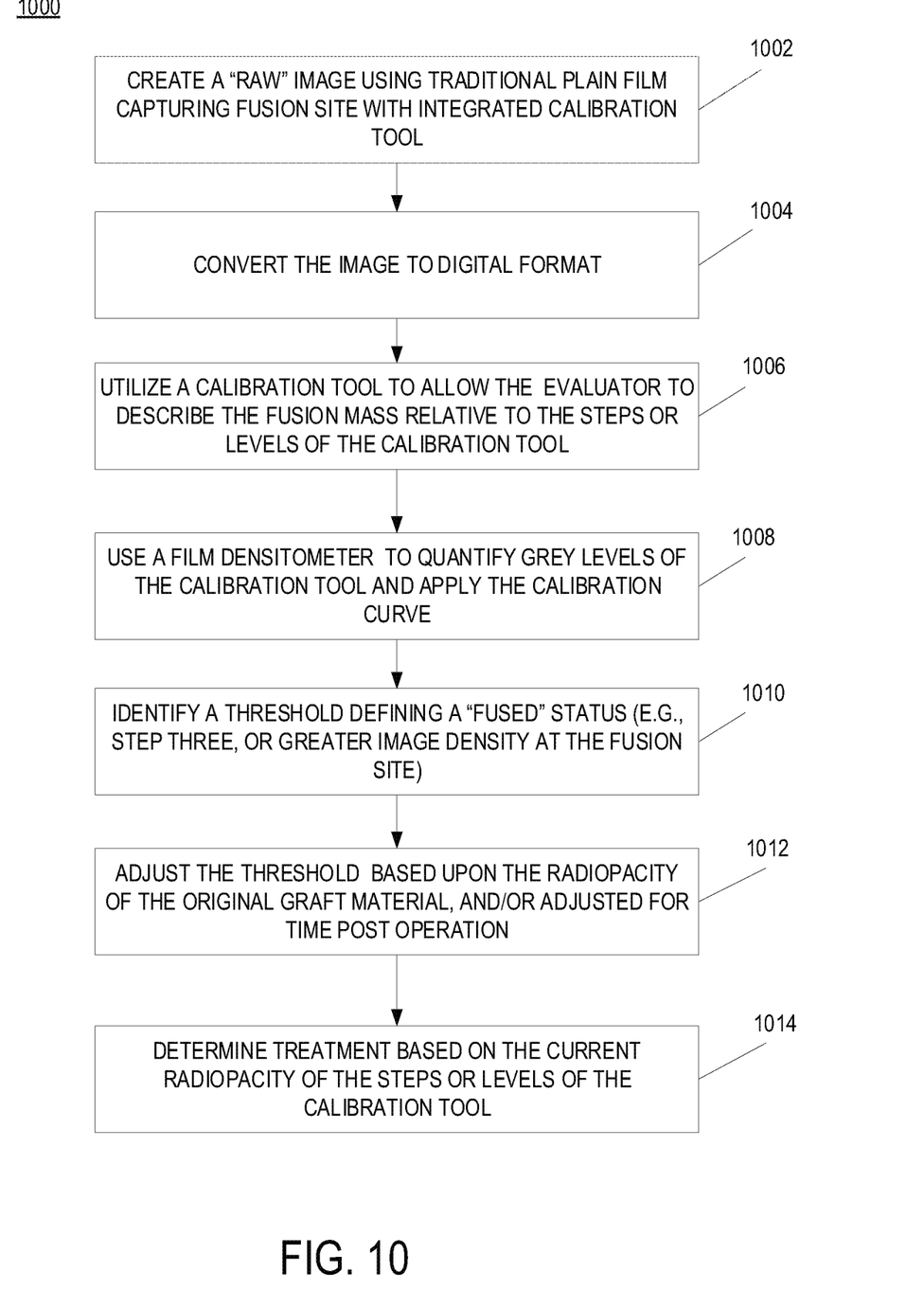
FIG. 10 is a flowchart of another method to calibrate clinical images of a fusion site.

FIG. 10 is a flowchart another embodiment of a method 1000 to calibrate clinical images of a fusion site. The method 1000 may include, at block 1002, creating a "raw" image using traditional plain film, digital X-ray, DEXA, or CT scanning technology. The "raw" image may include three-dimensional image that are reconstructed radiographic images from CT scans. The image may be a radiograph that may be a traditional film radiograph assessed by densitometry. The image may be a traditional film radiograph that is scanned and converted to digital format before calibration and assessment. The image may be captured digitally from the radiographic equipment. The method 1000 may include, at block 1004, converting the "raw" image to a digital format, if required. The method 1000 may include, at block 1006, utilizing the integrated calibration tool to allow the surgeon or other evaluator to describe the fusion mass relative to the steps (graded radiopacity) of the calibration tool. The method 1000 may include, at block 1008, using a film densitometer to quantify grey levels and apply the calibration curve.

The method 1000 may include, at block 1010, identifying a threshold defining a "fused" status (e.g., step or level three, or greater image density at the fusion site). The method 1000 may include, at block 1012, adjusting the threshold based upon the radiopacity of the original graft material, and/or adjusted for time post operation.

The block 1010, generally determines the degree of bone maturity, strength, osteoporotic state, or other features of healing or degrading bone tissue based on a comparison of a bone at the site in the image and any one graded level (grey level) of radiopacity.

The processes for calibrating the digital images may use the calibration tools, step wedge, or other graded radiopaque feature beneath the patient's tissue at the approximate level of the fusion mass.

The embodiments herein may include the use of an improved calibration tool. The calibration tool may be placed in such a way that it receives similar irradiation to that of the fusion site. Since the prior wedges were generally not implanted in the body, they did not achieve the goals of the herein disclosed inventions. For example, if the wedge is at a different radiographic plane than the fusion mass, and is affected by beam falloff at the edges and the incongruent tissue thicknesses between the site of interest and the site of the wedge.

Accordingly, the scenarios herein place the step wedge inside of the patient, at the approximate depth of the fusion mass. The calibration step wedge can be integrated into an implant used in spinal surgery, and placed by a surgeon into an appropriate anatomic position.

Clinically, surgeons typically will take AP and Lateral films, which they use to assess fusion progress. In use, the implant of certain embodiments of the invention may be approximately orthogonal to the radiation beam (within a small error), in order to avoid shadowing or projection effect errors associated with out-of-plane images. To facilitate orienting the irradiation beam relative to the implant, an orientation feature (FIGS. 5A-5B) can be incorporated into the implant. In the illustration of FIGS. 5A-5B, the guide or orientation feature 515 may be similar to the sights of a rifle, achieving orientation when the ridge at one end is aligned with the groove in the opposite end.

The implant devices with integrated calibration tool with graded radiopacity provides a means to remove image variation due to patient factors. The implant devices with integrated calibration tool provides a means to remove image variation due to imaging parameters. The implant devices with integrated calibration tool with graded radiopacity may provide a means to calibrate images for comparison across time in the same individual patient. This permits a clinician to track progression of healing of the fusion mass, and to identify when the fusion has reached a minimum criteria for loadbearing, activities of daily living, rod removal, or other conditions. The implant devices with integrated calibration tool with graded radiopacity may further provide a means to calibrate images for comparison between individual patients, as in, e.g. a clinical study or trial. The implant devices with integrated calibration tool with graded radiopacity may also provide an objective assessment of fusion status (fused/not fused) for use in clinical practice and clinical research studies. The implant devices with integrated calibration tool with graded radiopacity can, in certain embodiments, provide a quantitative, calibrated measurement of bone mineral content and bone mineral density to allow fusion mass progression to be quantified over time.

The integrated calibration tool may be configured to provide a quantitative assessment of maturation and a "minimum criteria for loadbearing." Accordingly, a clinician may be able to quantify progression of healing to establish timelines for returning-to-work by the patient. The integrated calibration tool may provide a quantitative assessment of fusion status and healing progression, which can be beneficial in clinical research outcomes. The integrated calibration tool may be useful in identifying states of progress in healing outside of the presence of symptoms.

A similar need for assessment of bone healing can occur in the context of a traumatic fracture or other break in other bony sites, where the bone should grow back together (called "union"). Surgeons may on occasion have cause for uncertainty as to the healing state.

A patient that is osteoporotic, for example, and who has previously received an implant containing the feature of the current invention, may be assessed for disease progression (i.e. bone loss) via calibrated images.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, one or more blocks of the described methods or techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 11:
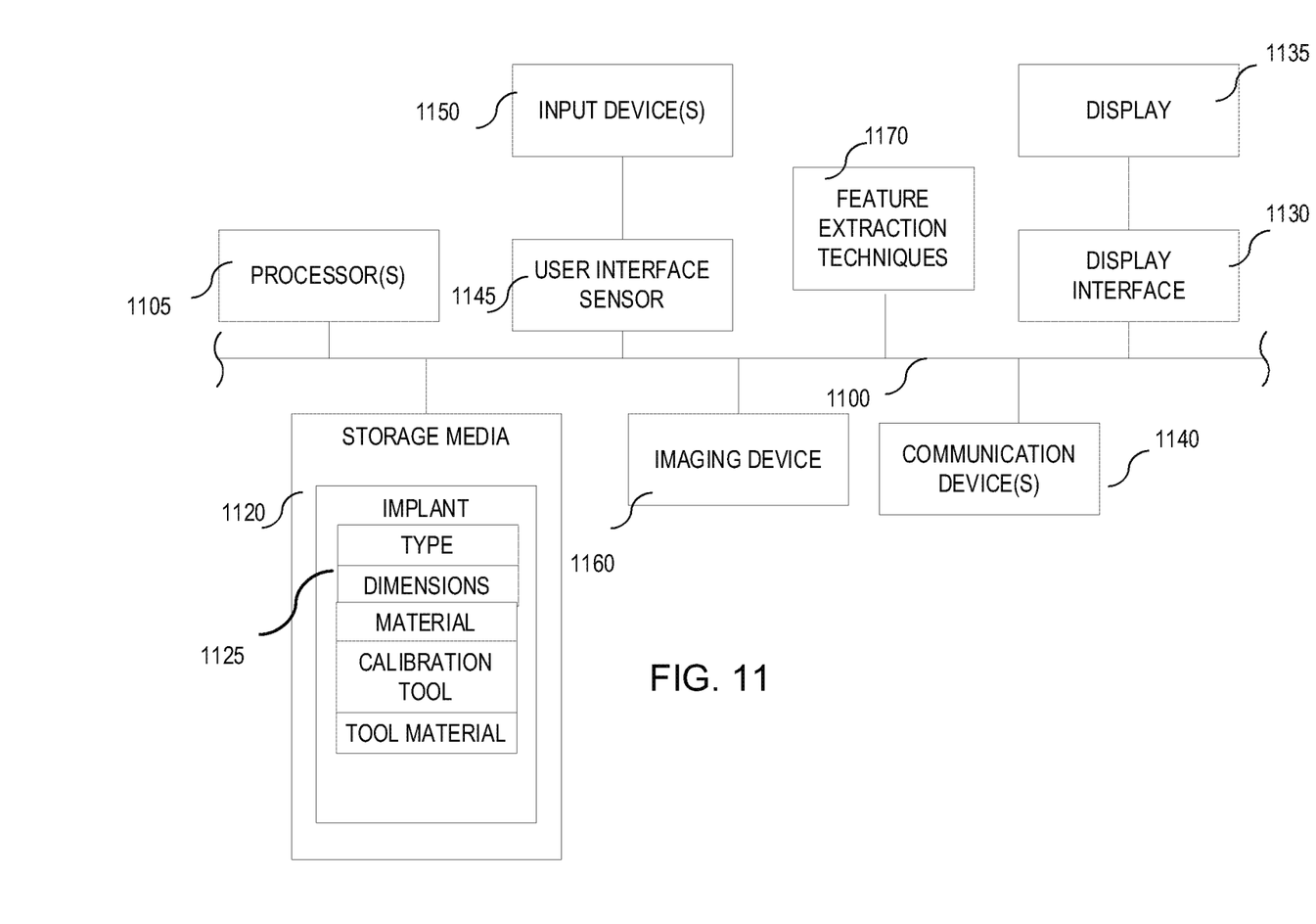
FIG. 11 is an example of internal hardware that may be included in any of the electronic components of an electronic device.

FIG. 11 depicts an example of internal hardware that may be included in any of the electronic components of an electronic device as described in this disclosure such as, for example, an on-premises electronic device, an associate electronic device, a remote electronic device and/or any other integrated system and/or hardware that may be used to contain or implement program instructions.

A bus 1100 can serve as the main information highway interconnecting the other illustrated components of the hardware in this embodiment. CPU 1105 is the central processing unit of the system, performing calculations and logic operations required to execute a program. CPU 1105, alone or in conjunction with one or more of the other elements disclosed in FIG. 11, is an example of a processor as such term is used within this disclosure. Read only memory (ROM) and random access memory (RAM) constitute examples of tangible and non-transitory computer-readable storage media 1120, memory devices or data stores as such terms are used within this disclosure. The memory device may store an operating system (OS) of the server or for the platform of the electronic device.

Program instructions, software or interactive modules for providing the interface and performing any querying or analysis associated with one or more data sets may be stored in the computer-readable storage media 1120. Optionally, the program instructions may be stored on a tangible, non-transitory computer-readable medium such as a compact disk, a digital disk, flash memory, a memory card, a universal serial bus (USB) drive, an optical disc storage medium and/or other recording medium. The program instructions may include instruction for performing feature extraction of a region of interest in the digitized images. The feature extraction algorithm 1170 may find the implant device and the graded radiopaque calibration tool. The storage media 1120 may include implant data 1125 which includes an implant type, implant dimension, and implant material. The implant data 1125 may include information associated with the calibration tool shape, size and type. The implant data 1125 may also include tool material used to form each level, marker or step of the calibration tool. The implant data 1125 may be used by the feature extraction algorithms or techniques to locate the implant device and interpret the grey level represented by the calibration tool in the pixels or voxels of the image.

An optional display interface 1130 may permit information from the bus 1100 to be displayed on the display 1135 in audio, visual, graphic or alphanumeric format. Communication with external devices may occur using various communication ports 1140. A communication port 1140 may be attached to a communications network, such as the Internet or an intranet. In various embodiments, communication with external devices may occur via one or more short range communication protocols. The communication port 1140 may include communication devices for wired or wireless communications via a communication link.

The hardware may also include an interface 1145, such as graphical user interface (GUI), which allows for receipt of data from input devices such as a keyboard or other input device 1150 such as a mouse, a joystick, a touch screen, a remote control, a pointing device, a video input device and/or an audio input device. The hardware may also include an imaging device 1160. The imaging device 1160 may be configured to capture one of one-dimensional (1D) images, two-dimensional (2D) images and three-dimensional (3D) images. For example, a 2D image may be captured by an X-ray or radiography machine. A 3D image may be captured by a CT scan machine. A 1D image may be captured by a Dual-energy X-ray absorptiometry (DEXA) machine. The imaging device 1160 may perform ionizing radiation. The imaging device 1160 may include an O-ARM™ Surgical Imaging System 2.0, by Medtronic Inc.

The imaging device 1160 may capture images by emitting energy or a frequency from two orthogonal planes. The received energy from the two orthogonal planes is used to develop a three-dimensional model of the fusion mass or fusion sight with the implant device. For 3D images, axial, coronal, sagittal and oblique slices may be captured. Imaging may take place up to 360° around the implant site, in increments or continuously (Spiral CT).

By way of non-limiting example, digital imaging processing may be deployed feature extraction techniques 1170 to extract out the implant device and/or the integrated graded radiopacity tool from a region of interest in the image.

In some embodiments, the image is collected digitally, and later processed to provide a calibrated image for fusion maturity assessment, for example. In other embodiments, the image should be digitized via standard digitization protocols.

In this document, "electronic communication" refers to the transmission of data via one or more signals between two or more electronic devices, whether through a wired or wireless network, and whether directly or indirectly via one or more intermediary devices. Devices are "communicatively connected" if the devices are able to send and/or receive data via electronic communication.

An "electronic device" or a "computing device" refers to a device or system that includes or shares a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions. Examples of electronic devices include personal computers, servers, mainframes, virtual machines, containers, cameras, tablet computers, laptop computers, media players and the like. Electronic devices also may include appliances and other devices that can communicate in an Internet-of-things arrangement. In a client-server arrangement, the client device and the server are electronic devices, in which the server contains instructions and/or data that the client device accesses via one or more communications links in one or more communications networks. In a virtual machine arrangement, a server may be an electronic device, and each virtual machine or container also may be considered an electronic device.

The terms "processor" and "processing device" refer to a hardware component of an electronic device that is configured to execute programming instructions. Except where specifically stated otherwise, the singular terms "processor" and "processing device" are intended to include both single-processing device embodiments and embodiments in which multiple processing devices together or collectively perform a process.

The terms "memory," "memory device," "data store," "data storage facility" and the like each refer to a tangible and non-transitory device on which computer-readable data, programming instructions or both are stored. Except where specifically stated otherwise, the terms "memory," "memory device," "data store," "data storage facility" and the like are intended to include single device embodiments, embodiments in which multiple memory devices together or collectively store a set of data or instructions, as well as individual sectors within such devices.

In this document, the terms "communication link" and "communication path" mean a wired or wireless path via which a first device sends communication signals to and/or receives communication signals from one or more other devices. Devices are "communicatively connected" if the devices are able to send and/or receive data via a communication link. "Electronic communication" refers to the transmission of data via one or more signals between two or more electronic devices, whether through a wired or wireless network, and whether directly or indirectly via one or more intermediary devices.

The features and functions described above, as well as alternatives, may be combined into many other different systems or applications. Various alternatives, modifications, variations or improvements may be made by those skilled in the art, each of which is also intended to be encompassed by the disclosed embodiments.

What is claimed is:

1. An implant device for use in achieving spinal fusion, the implant device comprising:
   an implant having an implant body; and
   a graded radiopacity calibration tool integrated with the implant body and having a plurality of sequentially increasing graded levels of radiopacity representative of a range of bone density parameter amounts, each level corresponding to a different bone density parameter amount.

2. The implant device according to claim 1, wherein:
   a smallest graded level of radiopacity is configured to appear slightly more visible than a background density of an image captured by ionizing radiation; and
   a largest graded level of radiopacity configured to appear as exceeding the range of the bone density parameter amounts.

3. The implant device according to claim 1, wherein:
   the graded radiopacity calibration tool is integrated into the implant body; and
   the plurality of sequentially increasing graded levels of radiopacity are configured to represent a grey level scale of from white to black or dark grey, in response to ionizing radiation.

4. The implant device according to claim 1, wherein the implant body is configured as one of a screw, intervertebral implant, a rod, a cross-brace, and a corpectomy device.

5. The implant device according to claim 1, wherein grading the radiopacity of each graded level of radiopacity occurs on one or more surfaces of the implant body.

6. The implant device according to claim 1, wherein the plurality of graded levels of radiopacity is made of composite materials, graded by material thickness to create a step wedge.

7. The implant device according to claim 6, wherein the composite material comprises one of boron nitride in polyether ether ketone (PEEK), Hydroxyapatite (HA) in PEEK, and osteoconductive PEEK, and composites of silicon nitride.

8. The implant device according to claim 1, wherein the plurality of sequentially increasing graded levels of radiopacity comprises different thicknesses of radiopaque implant material, wherein each graded level corresponds to a different thickness.

9. The implant according to claim 8, wherein the graded radiopacity calibration tool comprises one of titanium, titanium alloys, cobalt chromium, tantalum, stainless steel, or alloys.

10. The implant device according to claim 1, wherein each level of the plurality of sequentially increasing graded levels of radiopacity comprises a radiopaque implant material having a different porosity.

11. The implant device of claim 1, wherein:
    the plurality of graded levels of radiopacity are configured, in response to ionizing radiation, to represent degrees of bone maturity, strength, osteoporotic state, state of healing, or state of degrading of bone tissue.

12. The implant device of claim 1, wherein the implant body further comprises an orientation guide to denote an image plane for image calibration, in response to ionizing radiation.

13. A method of measuring fusion of adjacent boney structures, the method comprising:
    capturing, in response to ionizing radiation generated by an imaging machine, an image of a fusion implant device at an implant site, the fusion implant device comprising:
    a graded radiopacity calibration tool having a plurality of graded levels of radiopacity representative of a range of bone density parameter amounts, each level corresponding to a different one bone density parameter amount;
    detecting, by a processor, a region of interest in the image, the region of interest including the fusion implant device and the plurality of graded levels of radiopacity in the image wherein the plurality of graded levels of radiopacity in the image configured to represent a grey level scale from white to black or dark grey, and
    determining an extent of a fusion process at the implant site based on the plurality of graded levels of radiopacity in the image.

14. The method according to claim 13, further comprising interpreting in the image fusion maturity in units of bone mineral density, bone mineral content, fusion status, fusion maturity, millimeters of calibration metal or houndsfield units.

15. The method according to claim 13, wherein the grey level scale of from white to black or dark grey represent degrees of bone maturity, strength, osteoporotic state, state of healing or state of degrading bone tissue.

16. The method according to claim 13, further comprising:
    detecting, by the processor, a smallest graded level of radiopacity configured to appear slightly more than a background density in the image captured by ionizing radiation;
    detecting, by the processor, a largest graded level of radiopacity configured to appear as exceeding the range of the bone density parameter amounts; and
    determine a degree of one of bone maturity, strength, osteoporotic state, state of healing and state of degrading bone tissue based on a comparison of a bone at the site in the image and radiopacity correlated from a calibration standardized curve defined by a standard, with a range of grey levels representative of degrees of one of the bone maturity, the strength, the osteoporotic state, the state of healing and the state of degrading bone tissue.

17. The method according to claim 13, further comprising:
    digitizing, by a processor, the captured image; and
    using a film densitometer to quantify the grey level scale in the captured image.

18. The method according to claim 17, further comprising:
    identifying a fused status threshold in the captured image based on the grey level scale.

19. The method according to claim 13, further comprising:
    digitizing, by a processor, the captured image into pixels;
    reading the pixels in the captured image at the region of interest; and generating a baseline of the grey level scale relative to one of the fusion implant device and the implant site.

20. The method according to claim 19, wherein the image is a baseline image; and further comprising, after generating the baseline:

capturing, in response to ionizing radiation generated by the imaging machine, a second image of the fusion implant device at the implant site comprising the graded radiopacity calibration tool having the plurality of graded levels of radiopacity;

detecting, by the processor, the region of interest including the fusion implant device and the plurality of graded levels of radiopacity in the image representative of the grey level scale; and comparing the grey level scale of the baseline image with the grey level scale of the second image.

21. The method according to claim 13, wherein the implant device is configured as one of a screw, intervertebral implant, a rod, a cross-brace, and a corpectomy device.

22. The method according to claim 13, wherein the grey level scale is represented in a step wedge.

\* \* \* \* \*